United States Patent
Jacquot et al.

(10) Patent No.: US 8,501,979 B2
(45) Date of Patent: Aug. 6, 2013

(54) METHOD FOR MANUFACTURING COMPOUNDS INCLUDING NITRILE FUNCTIONS

(75) Inventors: Roland Jacquot, Francheville (FR); Philippe Marion, Vernaison (FR)

(73) Assignee: Rhodia Operations, Aubervilliers (FR)

(*) Notice: Subject to any disclaimer, the term of this patent is extended or adjusted under 35 U.S.C. 154(b) by 165 days.

(21) Appl. No.: 13/132,964

(22) PCT Filed: Nov. 26, 2009

(86) PCT No.: PCT/EP2009/065872
§ 371 (c)(1),
(2), (4) Date: Jul. 29, 2011

(87) PCT Pub. No.: WO2010/063632
PCT Pub. Date: Jun. 10, 2010

(65) Prior Publication Data
US 2011/0288324 A1 Nov. 24, 2011

(30) Foreign Application Priority Data
Dec. 4, 2008 (FR) .................................... 08-58264

(51) Int. Cl.
*C07C 253/00* (2006.01)
*C07C 63/30* (2006.01)
(52) U.S. Cl.
USPC .......................................... 558/311; 564/490

(58) Field of Classification Search
USPC ........................................... 558/331; 564/490
See application file for complete search history.

(56) References Cited

U.S. PATENT DOCUMENTS

| 3,242,204 | A | * | 3/1966 | Decker et al. | 558/311 |
| 3,393,222 | A | * | 7/1968 | Schwarz et al. | 558/311 |
| 4,743,702 | A | * | 5/1988 | Hoelderich et al. | 558/311 |
| 6,005,134 | A | * | 12/1999 | Terasaka et al. | 558/311 |
| 7,259,274 | B2 | * | 8/2007 | Terasaka et al. | 558/311 |
| 2005/0059836 | A1 | | 3/2005 | Terasaka et al. | |

FOREIGN PATENT DOCUMENTS

| GB | 797945 A | 7/1958 |
| GB | 1397729 A | 6/1975 |

OTHER PUBLICATIONS

International Search Report dated Apr. 22, 2010 issued in International Application No. PCT/EP2009/065872.
Cope et al., "Azelanitrile", Organic Synthesis, Coll. vol. 4, p. 62 (1963); vol. 34, p. 4 (1954).

* cited by examiner

*Primary Examiner* — Nyeemah A Grazier
(74) *Attorney, Agent, or Firm* — Dentons US LLP

(57) ABSTRACT

A process for the preparation of compounds containing nitrile functions and, more specifically, compounds containing two nitrile functions, such as succinonitrile and adiponitrile, is described. A process for preparing dintrile compounds obtained by reacting ammonia with an aqueous solution of a dicarboxyl compound in the presence of a silicon orthophosphate catalyst is also described.

12 Claims, No Drawings

METHOD FOR MANUFACTURING COMPOUNDS INCLUDING NITRILE FUNCTIONS

This application claims priority under 35 U.S.C. §119 of FR 0858264, filed Dec. 4, 2008, and is the United States national phase of PCT/EP2009/065872, filed Nov. 26, 2009, and designating the United States (published in the French language on Jun. 10, 2010, as WO 2010/063632 A1; the title and abstract were also published in French), each hereby expressly incorporated by reference in its entirety and each assigned to the assignee hereof.

The present invention relates to the preparation of compounds containing nitrile functions, more preferably of compounds containing two nitrile functions, such as succinonitrile and adiponitrile.

It relates more particularly to the preparation of compounds containing nitrile functions from compounds containing carboxyl functions which are, advantageously, present in fermentation media or fermentation liquors.

Compounds containing nitrile functions, and especially dinitrile compounds such as adiponitrile and succinonitrile, are products which are important in the manufacture of amine compounds or polymers, for example.

For instance, adiponitrile is an important compound used as an intermediate in the manufacture of hexamethylenediamine, or of epsilon-caprolactam. These two compounds are monomers which are used in the manufacture of polyamides, especially polyhexamethylenediamine adipamide (PA 6,6) or polycaproamide (PA 6). Hexamethylenediamine is also used for the synthesis of diisocyanates, which are important monomers in the manufacture of polyurethanes.

Adiponitrile and succinonitrile may also be used in processes for manufacturing polyamides by condensation reaction with diacid monomers.

Numerous processes have been proposed for synthesis of adiponitrile. These processes principally use, as their starting material, hydrocarbon compounds obtained from the refining of petroleum. Thus the main processes for synthesis of adiponitrile are the hydrocyanation of butadiene, and the ammoxidation of propane or of propene.

Also exploited has been a process for preparing adiponitrile by converting adipic acid into adiponitrile in the presence of ammonium hydroxide. This process is described particularly in French patents 2028842, 2132849 and 2144340.

In this process, the adipic acid used as starting material was obtained from a hydrocarbon, such as cyclohexane, which was obtained during the refining of petroleum.

In view of the exhaustion of petroleum resources, many research studies have been undertaken with the aim of developing processes for synthesizing these important compounds in the manufacture of materials that are used in numerous applications, starting from renewable raw materials or resources. Generally speaking, these renewable resources are composed of cultivated or uncultivated plant material, such as trees and plants such as sugar cane, maize, manioc, wheat or the like.

This plant material is converted by processes which generally comprise a plurality of mechanical, chemical and biological steps into compounds which belong to the class of sugars, such as glucose, sucrose, fructose or the like. The resulting sugars are then converted, advantageously, by processes such as fermentation into compounds containing particular organic functions. Hence, by a process of biological fermentation, it is possible to convert the sugars into compounds containing carboxyl functions. These fermentation processes produce aqueous solutions of organic compounds that are referred to as fermentation liquors.

One of the objects of the invention is to provide a process for preparing compounds comprising at least one nitrile function, using as starting material, preferably, an aqueous solution of a carboxyl compound, and, even more advantageously, the aqueous solutions referred to as fermentation liquors that are obtained by fermentation of sugars produced by the transformation of renewable resources.

For this purpose, the invention provides a process for preparing compounds of general formula I:

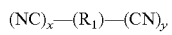

in which
$R_1$ represents a saturated or unsaturated, linear or branched hydrocarbon group containing 1 to 20 carbon atoms and possibly containing heteroatoms, and
x and y represent 0 or 1, with (x+y) being 1 or 2.

This process involves reacting ammonia with a salt of an organic diacid of general formula II

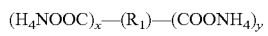

in which x, y and $R_1$ have the meaning indicated above, in the presence of a catalyst comprising a crystalline silicon orthophosphate.

The process is implemented at a temperature of between 300° C. and 450° C., preferably between 350° C. and 425° C.

The aqueous solution of compounds of formula II is evaporated before being contacted with the catalyst, either in an evaporation device or by spraying into the stream of superheated ammonia. These two means of evaporating the aqueous solution are given solely as indicators.

In another feature of the invention, the catalyst comprises less than 5% by weight of amorphous silicon orthophosphate.

In another feature of the invention, the compound of general formula II is an aqueous solution. This aqueous solution is obtained more advantageously in a process of biological transformation of a solution containing sugars that is itself obtained from a process of transformation or extraction using, as starting materials, essentially plant materials which constitute a renewable resource.

This aqueous solution obtained from a process of biological transformation is obtained, for example, by a sugar fermentation process. This medium is referred to generally as "fermentation liquor".

These fermentation liquors may be used directly or after filtration to separate the biological material or biomass from the medium. As an example of a process for preparing fermentation liquors that are suitable as starting material for the process of the invention, mention may be made of the processes described in the article by Varadarajan et al. that appeared in Biotechnol. Pro. 1999, 15, 845-854, or the article by Olson et al. that appeared in Applied Biochemistry and Biotechnology 2003, Vol. 105-108, 843-851.

The aqueous solutions and/or fermentation liquors that are suitable for the process of the invention have a weight concentration of compounds of general formula II that is generally greater than 1% by weight, preferably between 1% by weight and 30% by weight, advantageously between 5% by weight and 25% by weight. However, the maximum concentration suitable is fixed by the solubility limit of the compound of formula II in water at the temperature at which the solution is fed into the evaporation device used to feed the solution onto the catalyst.

This concentration may be obtained directly by the process of biological fermentation, or by concentration of the fermentation liquor or of the aqueous solution, for example, by evaporation of water. The compound of general formula II is advantageously selected from the group consisting of ammonium succinate, ammonium adipate, ammonium glutamate, ammonium glutarate, ammonium salts of difunctional fatty acids, ammonium hexadecanedioate or the like.

A catalyst suitable for the invention may be obtained advantageously by impregnating a silica with phosphoric acid in aqueous solution, then calcining in air, to form silicon orthophosphate. The calcining temperature is advantageously between 450° C. and 800° C., for example between 450° C. and 550° C. A preparation process of this kind is described more particularly in French patent application 2810317.

It is also possible to use catalysts which are sold by a number of companies such as the company UOP. However, it may be necessary to treat these commercial catalysts in order to increase the level of crystalline form, by a heat treatment, for example.

The catalyst is generally in solid form, for example in the form of beads, cylindrical extrudates, honeycomb or the like. The catalyst is disposed in a reactor in the form of a fixed bed through which the fermentation liquor and the ammonia in vapour form are passed.

The catalyst of the invention may further comprise dopant elements or cocatalysts.

In another feature of the invention, the catalyst used for implementing the process of the invention may be regenerated by treating the catalyst bed with air at a temperature of between 450 and 500° C. for 10 to 20 hours. The regeneration treatment may be monitored by detecting the presence of $CO_2$ in the air at the reactor outlet. Treatment is halted when the absence of $CO_2$ in the air is found. The catalyst thus regenerated may be used for further implementation of the process of the invention, with equivalent catalytic performance.

The vapours recovered at the reactor outlet are condensed for the purpose of recovering the compound containing the nitrile functions. These compounds may be subsequently purified, by conventional techniques such as distillation, crystallization, extraction or the like.

The catalyst is advantageously activated in particular by treatment with gaseous ammonia at a temperature of between 350° C. and 500° C., before the feeding of the aqueous solution of compound II.

Further details and advantages of the invention will emerge more clearly from a reading of the examples which are given below solely by way of indication.

The reaction is implemented in gaseous phase at a temperature in the region of 400° C. and under atmospheric pressure. The catalyst used is composed of silicon orthophosphate of formula $Si_3(PO_4)_4$.

This catalyst is prepared by impregnating a silica with 85% phosphoric acid and then calcining in air at 500° C.

EXAMPLE 1

Preparation of Succinonitrile

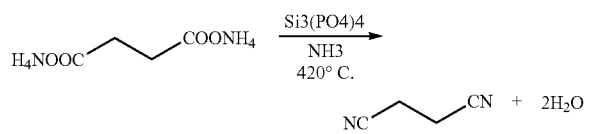

The starting material is an aqueous solution containing approximately 10% to 20% by weight of ammonium succinate in solution in water.

This aqueous solution contains other acids and diacids containing fewer carbon atoms, which are referred to as "lower acids".

The composition of the aqueous solution used corresponds to the composition of a solution or fermentation liquor obtained from a process of fermentation of a medium containing sugars obtained from the treatment of a plant material.

The solubility of the ammonium salts of these acids increases greatly with temperature, and so it may be of advantage to use a hot solution in order to prevent crystallization problems.

A glass reactor with a diameter of 22 mm is supplied in succession with
3 ml of glass powder
5 ml (4.0 g) of $Si_3(PO_4)_4$ catalyst in the form of extrudates
3 ml of glass powder.

The catalyst bed is activated first by treatment at 500° C. in a stream of air of 3 l/h for approximately 15 hours, followed, after lowering of the temperature to 420° C., by replacement of the air by a stream of $NH_3$ at a rate of 1.5 l/h.

Using a syringe driver, an aqueous solution of ammonium succinate at a concentration of 15% by weight is injected at a rate of 6 ml/h. Under these conditions, the molar $NH_3$/ammonium succinate ratio is 10.

The condensates are recovered and analysed by gas chromatography (GC).

After injection of aqueous solution for 4 hours, the yield of conversion to succinonitrile relative to the ammonium succinate introduced is 65%.

EXAMPLE 2

Preparation of Succinonitrile from Succinic Acid

Example 1 is repeated, but using a 20% strength by weight aqueous solution of succinic acid.

The catalyst bed is identical to that of the preceding test. Following activation, a stream of ammonia at 2 l/h is passed over the catalyst bed, and, at the same time, the aqueous solution of succinic acid is injected at a rate of 4 ml/h.

Under these conditions, the molar $NH_3$/succinic acid ratio is 10. The condensates are recovered and analysed by GC.

After 5 hours of injection, the yield of succinonitrile is 70%.

EXAMPLE 3

Preparation of Adiponitrile

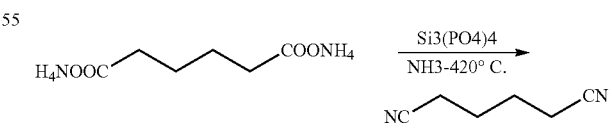

Example 1 is repeated, replacing the ammonium succinate solution with a 15% strength by weight ammonium adipate solution. A stream of $NH_3$ at 1.5 l/h is injected into the catalyst bed, and the hot aqueous ammonium adipate solution is injected at a rate of 4 ml/h.

After 4 hours of injection, the yield of conversion of ammonium adipate to adiponitrile is 72%.

EXAMPLE 4

Preparation of Succinonitrile with Regenerated Catalyst

When the performance of the catalyst bed falls below the economic optimum, the bed can be regenerated in accordance with the following procedure, which is described solely by way of example.

The feed to the catalyst bed of ammonia and aqueous ammonium carboxylate solution is halted. The catalyst bed, maintained under a stream of nitrogen, is cooled to ambient temperature. The stream of nitrogen is replaced with a stream of 3 l/h of air, and the catalyst bed is heated gradually to 500° C. Treatment in air at 500° C. is maintained for approximately 15 hours. The presence of $CO_2$ in the exiting air is detected, and the treatment is continued until $CO_2$ is no longer detected in the outgoing flow.

The temperature of the catalyst bed is brought to 420° C., the flow of air being replaced by a stream of nitrogen at 3 l/h. At 420° C., the stream of nitrogen is replaced gradually by ammonia. The catalyst is then regenerated, and a succinonitrile production test was carried out in accordance with the procedure described in Example 1. The conversion yield obtained is identical.

The invention claimed is:

1. A process for preparing a compound, the process comprising preparing the compound to have a general formula I $$(NC)_x-R_1(CN)_y \quad (1)$$

in which:

R$_1$ represents a saturated or unsaturated, linear or branched hydrocarbon group containing 1 to 20 carbon atoms and optionally containing hetero-atoms, x and y are 0 or 1, with (x+y) being 1 or 2, by reacting ammoniac with a compound of general formula II $$(H_4NOOC)_x-(R_1)-(COONH)_y$$

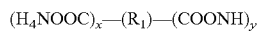

in vapour phase in the presence of a catalyst comprising a silicon ortho phosphate of formula $Si_3(PO_4)_4$, at a temperature of between 300° C. and 450° C.

2. The process according to claim 1, wherein the compound of general formula II is in aqueous solution.

3. The process according to claim 2, wherein the compound of general formula II in the aqueous solution is present in a concentration of greater than 1% by weight.

4. The process according to claim 3, wherein the compound of general formula II in the aqueous solution is present in a concentration of between 1% and 30% by weight.

5. The process according to claim 2, wherein the aqueous solution of the compound of general formula II is a medium resulting from a biological transformation of a sugar compound.

6. The process according to claim 5, wherein the medium obtained from the biological transformation that is used is obtained after separation from a biomass.

7. The process according to claim 1, wherein the compound of general formula II is selected from the group consisting of ammonium succinate, ammonium adipate, ammonium glutamate, ammonium glutarate, ammonium salts of fatty diacids, ammonium hexadecanedioate and combinations thereof.

8. The process according to claim 1, wherein the reaction is performed in a reactor comprising a fixed catalyst bed.

9. The process according to claim 1, wherein the catalyst is obtained by impregnating a silica with phosphoric acid and calcining in air.

10. The process according to claim 9, wherein the calcining is performed at a temperature of between 400° C. and 800° C.

11. The process according to any of the claim 1, wherein the compound of general formula I is selected from the group consisting of adiponitrile and succinonitrile.

12. The process according to claim 4, wherein the concentration of the compound of the general formula II in the aqueous solution is between 1% and 2% by weight.

* * * * *